Figure 1:
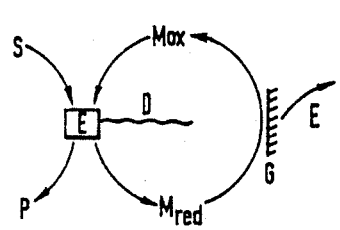

United States Patent [19]

Hill et al.

[11] Patent Number: 4,840,893

[45] Date of Patent: Jun. 20, 1989

[54] ELECTROCHEMICAL ASSAY FOR NUCLEIC ACIDS AND NUCLEIC ACID PROBES

[75] Inventors: Hugh A. O. Hill; Susan I. Libor, both of Oxford, England

[73] Assignee: Medisense, Inc., Cambridge, Mass.

[21] Appl. No.: 769,629

[22] PCT Filed: Dec. 14, 1984

[86] PCT No.: PCT/GB84/00432

§ 371 Date: Oct. 15, 1985

§ 102(e) Date: Oct. 15, 1985

[87] PCT Pub. No.: WO85/02627

PCT Pub. Date: Jun. 20, 1985

[30] Foreign Application Priority Data

Dec. 16, 1983 [GB] United Kingdom ............... 8333650
Dec. 16, 1983 [GB] United Kingdom ............... 8333651
Jan. 19, 1984 [GB] United Kingdom ............... 8401399

[51] Int. Cl.$^4$ .................. C12P 1/68; G01N 33/53; G01N 33/566; C07H 19/06

[52] U.S. Cl. .......................................... 435/6; 435/7; 435/18; 435/25; 435/26; 435/28; 435/810; 435/817; 436/501; 436/537; 436/806; 436/904; 536/26; 536/27; 536/28; 935/77; 935/78

[58] Field of Search ............... 435/6, 7, 91, 14, 18, 435/19, 25, 26, 28, 817,810; 436/501, 806, 518, 586, 537, 808, 149, 151, 909; 935/77-78; 536/26, 27, 28

[56] References Cited

U.S. PATENT DOCUMENTS

| 4,233,144 | 11/1980 | Pace et al. ............... 436/806 X |
| 4,287,300 | 9/1981 | Gibbons et al. ............... 436/806 X |
| 4,563,417 | 1/1986 | Albarella et al. ............... 435/6 |
| 4,591,550 | 5/1986 | Hafeman et al. ............... 435/4 |
| 4,704,353 | 11/1987 | Humphries et al. ............... 435/4 |
| 4,711,245 | 12/1987 | Higgins et al. ............... 128/635 |

FOREIGN PATENT DOCUMENTS

0078636  5/1983  European Pat. Off. .
0125139  11/1984  European Pat. Off. .
0150999  8/1985  European Pat. Off. .

OTHER PUBLICATIONS

Koval, C. et al., Analytical Chem, 50 No. 2: 223-227 (1978).

Clarke, M. et al., Jour Amer Chem Soc., 97 No. 6: 1397-1403 (1975).

*Primary Examiner*—Robert J. Warden
*Assistant Examiner*—Jack Spiegel

[57] ABSTRACT

The present invention discloses an assay for nucleic acid which comprises the steps of;
(a) providing a probe material comprising;
  (i) a sequence of nucleic acids complementary to a given target sequence and,
  (ii) a first ligand chemically linked thereto and capable of a specific binding reaction with an antiligand;
(b) contacting the said probe material with an assay system comprising:
  (i) a suitable mediator, enzyme, substrate system capable of transferring charge to an electrode surface when the enzyme is catalytically active, and;
  (ii) a second ligand chemically linked to one of said mediator, enzyme or substrate, wherein the second ligand is capable of a competitive binding reaction with the antiligand, and;
  (iii) the said antiligand, whereby the said first ligand competes with the said second ligand in a specific binding reaction with the antiligand, and;
(c) contacting the above system with a solution suspected of containing the said target sequence whereby the binding of any of the said target sequence present to the probe affects the availability of the first ligand and therefore alters the rate of charge transfer to the electrode.

47 Claims, 3 Drawing Sheets

Cyclic Voltamogram of Biotin Cytochrome C and Horseradish Peroxidase

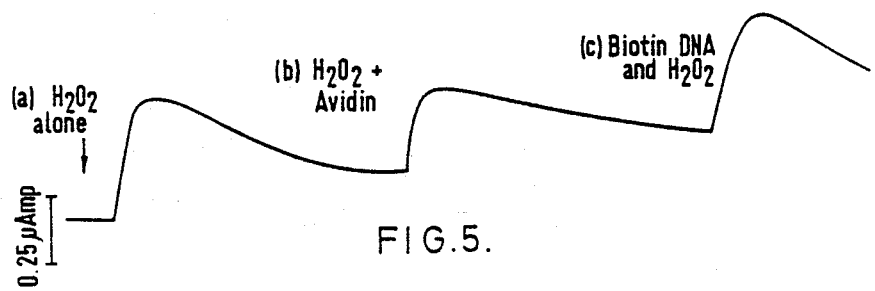
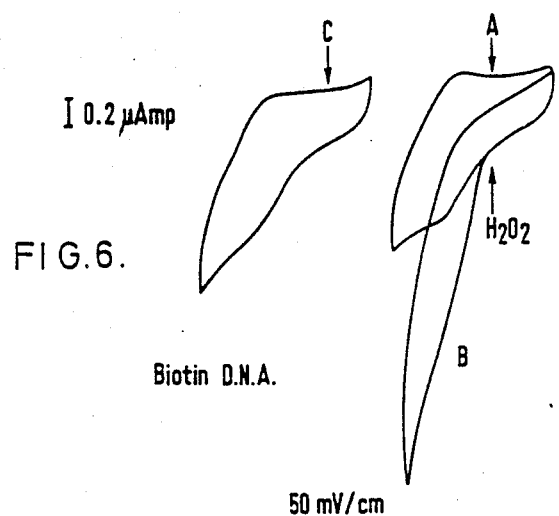

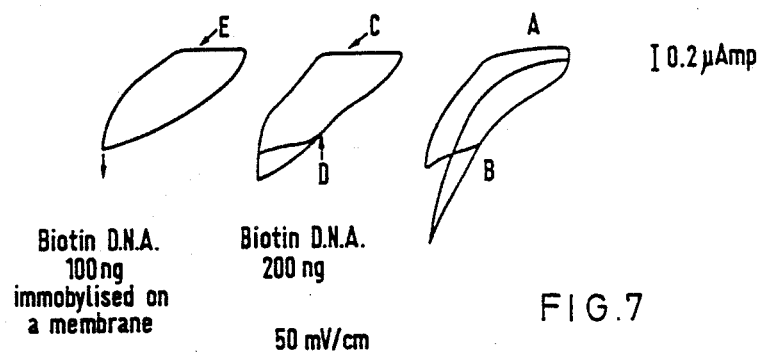
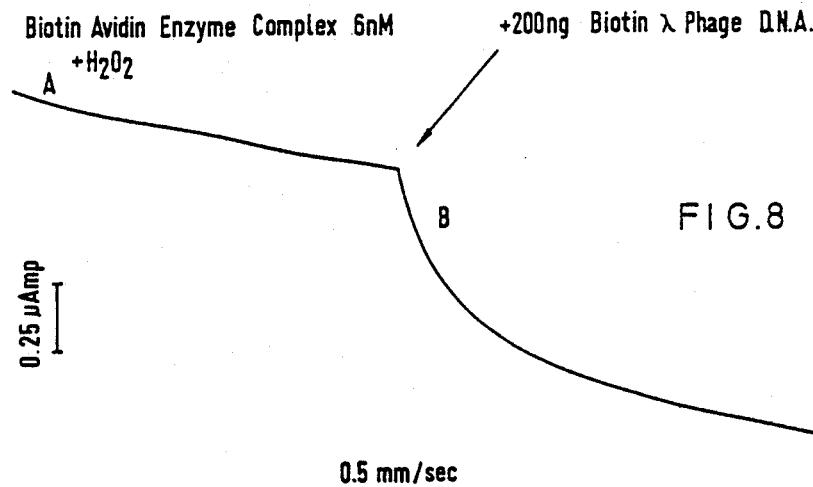

ELECTROCHEMICAL ASSAY FOR NUCLEIC ACIDS AND NUCLEIC ACID PROBES

The present invention is concerned with assays for nucleic acids, the said assays extending to both detection of the presence f nucleic acids and to the particular identification of specific nucleic acid molecules.

There is a particular need in many areas of biochemical research and commerce to be able to assay for the presence of nucleic acids in a sample, and further, to assay for the existence of particular sequences within the said nucleic acids.

The exploitation of the hybridisation between two single-stranded DNA or RNA molecules which have a complementary sequence has been one approach to this problem. Molecules for use in such assays, which are capable of binding to a DNA or RNA sequence which is defined to a particular level of homology, are known as DNA-probes.

Known DNA (RNA) probe techniques share a similarity in that the DNA (RNA) polymer is not readily detectable by its inherent biochemical activity. It is therefore necessary to mark the polymer with some signal-producing chemical or biochemical species, such methods as are presently known include the followin prior art:

PRIOR ART

Avidin-Biotin Reaction; this technology relies on the affinity of the egg-white glycoprotein avidin for biotin. Biotin (Vitamin H) can be covalently linked to the nucleotide residues which comprise the monomeric subunits of the DNA polymer. The modified subunits can still undergo the classical binding reaction between complementary strands of double-stranded DNA, and thus can be incorporated into synthetic DNA probes. At present, to detect the presence of such probes which have formed short double-stranded regions after exposure to complementary sample DNA, the unbound probe must first be separated from the sample DNA/-bound probe complex. This is normally done by performing the binding reaction in conditions under which the sample DNA is immobilized on a substrate and washing, although centrifugation may perform the same function. The bound probe is detected by the addition of avidin to which either a fluorescent- marker-labeled antibody or an enzyme has been attached.

One problem with the above method is that small oligonucleotide probes (20 nucleotides) contain only a small number of biotinylated sites, limiting the amount of avidin which can be bound. Attempts have been made, with some success, to add long "tails" of up to several thousand bases to the probe DNA, in which case only the tail need be labeled. The method can detect up to a resolution of $10^{-13}$ g of DNA, or about $10^5$ copies of a single gene. Although originally the marker on the avidin was horse radish peroxidase the method has now been extended to include alkaline phosphatase. Unfortunately the method is generally difficult to establish for a new diagnostic scheme as either the biotin-linked probe DNA is difficult to prepare or the labeled tail interferes with sensitivity.

Use of Mediators

Commonly owned European Patent Application No. 84303090.9 published on Nov. 14, 1984 as EP No. 125139A discloses a method in which at least one of a mediator and an enzyme are chemically linked to a nucleic acid probe sequence whereby specific binding of the probe sequence to the target sequence in a single-strand nucleic acid material to be investigated affects the electrochemical availability of the chemically linked species as detected by a sensor electrode in presence of the enzyme substrate, whereby the presence of the target sequence can be detected.

As disclosed in the specification, the nucleic acid sequence can be RNA e.g. messenger RNA but is usually DNA.

A suitable method for the practice of this technique has been given as follows;
(a) providing a single strand nucleic acid material to be investigated for a given target sequence;
(b) selecting a probe material with a sequence of nucleic acids complementary to the target sequence;
(c) choosing a procedure from among;
  (i) chemically linking the probe with an enzyme and adding the enzyme-linked probe to a solution containing both a substrate for the enzyme and a mediator,
  (ii) chemically linking the probe with a mediator and adding the mediator-linked probe to a solution containing both a substrate and an enzyme for the said substrate;
  (iii) chemically linking the probe with a mediator/enzyme combination and adding the so-modified probe to a solution containing a substrate for the enzyme;
(d) contacting the solution containing the chemically linked probe sequence with a sensor electrode whereby charge is transferred by the mediator to the electrode from the enzyme-catalysed substrate reaction; and
(e) contacting the solution with the single stranded material,
whereby alteration in the amount of charge transferred is an indication of a specific binding reaction between the probe and target affecting the availability of enzyme, mediator or combination.

The probe material can be a naturally occuring DNA fragment or a synthetically produced material.

Alterations in the sequence of steps can be readily envisaged. Also the sensor electrode itself can include the mediator or the enzyme, although generally it is preferred for the probe sequence and the target sequence both to be present in solution.

The mediator can be linked indirectly to the probe sequence by a linker group, and a material reactive to the linker groups can be present on the electrode. In this case the whole complex is present on the electrode; when a target sequence is present, and binds to the probe sequence, an alteration in electrode current is produced.

Mediators Disclosed

The use of ruthenium complexes on a graphite electrode is disclosed in Koval and Anson [Analytical Chemistry, Vol 50, 223 (1978)] in which the following ruthenium complexes are discussed;
$Ru(NH_3)_6^{3+,2+}$
$Ru(NH_3)_5py^{3+,2+}$
$Ru(NH_3)_5L^{3+,2+}$
Where L is pyridine, 4-aminomethylpyridine (AMP), or N-(4-picolinic)-benzamide (PBA)
$Ru(NH_3)_5OH_2^{3+,2+}$
$Ru(NH_3)_5Cl^{3+,2+}$

Errors of Metabolism

One aim of the DNA probe technology and the enzyme detection/assay technology so far developed, has been to detect inbuilt errors of metabolism which lead to a variety of "genetic diseases" and inheritable disorders. Among such disorders are: familial Goiter (iodotyrosine dehalogenase defective), Maple syrup urine disease (alpha-keto decarboxylase defective), Xanthinuria (Xanthine oxidase defective) and Methaemoglobinemia (Methaemoglobin reductase defective). A full list of 3500 conditions due to defective genes can be found in McKusick's "Mendelian Inheritance in Man".

One particular disease of interest is sickle-cell anaemia, in which one of the normal globin gene codons corresponding to the fifth, sixth and seventh amino acids of a particular chain are not, as normal CCT-GAG-GAG, but read CCT-GTG-GAG, thereby replacing valine for glutamic acid at position six. Synthetic oligonucleotides have been made which can act as probes for the sequence variation in prenatal diagnosis of the disease, and successfully distinguish between the wild type and the abberant gene. Assay of the components of the binding mixture was performed by a radioactive tracer method. A similar approach has been taken with the point mutation reported to cause antitrypsin deficiency.

As can be seen from the above, however, the methods of detailed metabolic assay presently available have certain disadvantages in that they require some or all of the following; short lifetime reagents (either radioactive, air-sensitive or light-sensitive), highly trained staff or (for autoradiography, ESR measurements or low-level light detection) expensive equipment.

Known methods of assay for binding reactions other than antigen/antibody and DNA/complementary DNA are generally similar to the above methods and suffer from similar problems.

According to one aspect of the present invention there is provided an assay for nucleic acid which comprises the steps of;
(a) providing a probe material comprising;
 (i) a sequence of nucleic acids complementary to a given target sequence and,
 (ii) a first ligand chemically linked thereto and capable of a specific binding reaction with an antiligand;
(b) contacting the said probe material with an assay system comprising;
 (i) a suitable mediator, enzyme, substrate system capable of transferring charge to an electrode surface when the enzyme is catalytically active, and;
 (ii) a second ligand chemically linked to one of said mediator, enzyme or substrate, wherein the second ligand is capable of a competitive binding reaction with the antiligand, and;
 (iii) the said antiligand,
 whereby the said first ligand competes with the said second ligand in a specific binding reaction with the antiligand, and;
(c) contacting the above system with a solution suspected of containing the said target sequence whereby the binding of any of the said target sequence present to the probe affects the availability of the first ligand and therefore alters the rate of charge transfer to the electrode.

By employing a method as described above, it is possible to perform the assay with an amplification step, thereby increasing the resolution of the assay.

Furthermore, the method of the present invention does not require the short-lived radioactive assay components which are employed in other types of assay.

Enzyme/substrate pairs whose electrochemical behaviour in association with mediator compounds have been studied by the Applicants include the following:

| Enzyme | Substrate |
|---|---|
| Flavo-proteins | |
| Pyruvate Oxidase | Pyruvates |
| L-Amino Acid Oxidase | L-Amino Acids |
| Aldehyde Oxidase | Aldehydes |
| Xanthine Oxidase | Xanthines |
| Glucose Oxidase | Glucose |
| Glycolate Oxidase | Glycolate |
| Sarcosine Oxidase | Sarcosine |
| Diaphorase | NADH |
| Glutathione Reductase | NADPH |
| PQQ Enzymes | |
| Glucose Dehydrogenase | Glucose |
| Methanol Dehydrogenase | Methanol and other Alkanols |
| Methylamine Dehydrogenase | Methylamine |
| Cytochrome b-linked Enzymes | |
| Lactate Oxidase | Lactate |
| Metalloflavoproteins | |
| Carbon monoxide Oxidoreductase | Carbon Monoxide |

It is believed that any of these enzyme-substrate pairs could be utilized in association with the mediator in the present invention, given some limitations on the assay conditions which would be obvious to the man skilled in the art. Of these pairs, it is clearly advantageous to utilise those enzyme/substrate pairs whose behaviour is established in most detail and which give good, preferably linear, response over the expected measurement range.

Ferrocenes (bis-cyclopentadienyl iron and its derivatives) have advantages over other mediators used with enzyme/substrate reactions for charge-transfer purposes.

The unique structure and properties of ferrocene (bis $n^5$ cyclopentadienyliron: $Fecp_2$) and its derivatives has resulted in a considerable amount of theoretical and experimental studies. First synthesised in 1951, ferrocene was the earliest example of the now well-known metallocene compounds.

Whilst ferrocenes, had been found to be of limited value in spectrophotometric assays as a result of their poor solubility in aqueous solution and low extinction coefficients, they have been found to be more suited to a bio-electrochemical system. Ferrocenes have:
(a) a wide range of redox potentials accessible through substitution of the cyclopentadienyl rings which can be functionalised;
(b) electrochemically reversible one-electron redox properties;
(c) a pH-independent redox potential and a slow autoxidation of the reduced form.

Within this general class of ferrocenes, i.e. the monomeric or polymeric derivates substituted around one or both rings, we have found certain individual ferrocenes such as are listed below:
1,1'-dimethylferrocene; acetic acid ferrocene; hydroxyethylferrocene; ferrocene;

1,1′ bis(hydroxymethyl)-ferrocene; monocarboxylic acid ferrocene; 1,1′-dicarboxylic acid ferrocene; chloroferrocene; and methyl trimethylaminoferrocene.

The E° values of various ferrocenes in phosphate buffer at pH 7.0 given in the above table, span a range of potentials, E°=100 to 400 mV vs SCE. The trend in E° values is in agreement with that expected on the basis of substituent effects. In general electron-donating groups stabilize the positive charge and hence promote oxidation more so than electron withdrawing groups.

Ferrocene derivatives which may be utilized in the method of the present invention are not to be considered as limited to the specific examples listed above, for example, the applicants have determined that ferrocene boronic acid, and ferrocene ethylamine exhibit mediator properties. Furthermore, the derivatives of ferrocene listed above may be further modified by suitable techniques known to the man skilled in the art, such as by treatment with nitrene, or diazo precursors.

Commonly owned European Patent Application No. 82305597.5, published as EP No. 078636 on May 5, 1983, describes and claims a sensor electrode composed of electrically conductive material and comprising at least at an external surface thereof the combination of an enzyme and a mediator compound which transfers electrons to the electrode when the enzyme is catalytically active.

The purpose of such an electrode is to detect the presence of, measure the amount of and/or monitor the level of one or more selected components capable of undertaking a reaction catalysed by the said enzyme.

Examples of electrode configurations, mediators and uses are given in that patent application.

This specification makes use of the chemical properties of the mediators and their derivatives as exemplified in our earlier patent applications.

This specification also makes use of the electrode structures and materials disclosed in the commonly owned European Patent Application No. 82305597.5, published as EP No. 078636 on May 5, 1983, included herein by reference, such as electrode materials selected from the group comprising; gold, platinum, silver, carbon or a one-dimensional conductor.

While the examples of mediator compounds given above are generally limited to the ferrocene group of mediators, the present invention may also employ the non-ferrocene mediators. Several classes of compounds may perform the functions of a mediator, that is transfer charge from an enzyme to an electrode surface (or in certain cases to a further enzyme).

Systems which have been studied have included the following mediator compounds;

Carbon-boron compounds (including the carboranes)
Viologens (N,N′-dialkyl of or diaryl derivatives of 4,4′-bipyridyl)
one-dimensional conductors (including the salts of TCNQ)
Phenazine dyes (including phenazine methosulphate and phenazine ethosulphate), and
Metalloporphyrins (including cytochrome-C)

However the preferred class of mediators are the transition metal complexes, particularly those in which the mediator comprises at least one, and preferably two organic rings, each of which is characterised by at least two double bonds that are conjugated and a metal atom in electron-sharing contact with each of the rings, since these have stability, exhibit rapid electron transfer reactions, have a wide range of redox potentials and are in many cases oxygen insensitive. The preferred mediators are generally those which have iron, nickel or ruthenium as the transition metals.

Although the preferable specific binding reaction in the method of the present invention is that between avidin (or streptavidin) and biotin, it should be noted that the invention is not to be taken as limited to this specific binding reaction but also extends to the following pairs of specific binding partners;
antigen and antibody,
hormone and receptor,
lectin and carbohydrate,
cofactor and enzyme, and,
nucleic acid and complementary nucleic acid.

The preferred method of determination of mediator in solution is by the use of cyclic voltametry as described variously in our above-mentioned patent applications, and as incorporated herein by reference. It should be noted that the complete cyclic voltammogram need not be taken in every case, and in many instances it is sufficient (as illustrated by example hereafter) to poise the cell at a particular potential and to make all current and/or voltage and/or time measurements at this potential. As above, the man skilled in the art will be conversant with such techniques and therefore they will not be described in detail herein.

According to a second aspect of the present invention there is provided a nucleic acid sequence probe for establishing the presence and/or copy number of a given sequence in a single-stranded nucleic acid molecule wherein a probe nucleic acid sequence is linked to;
(a) either a mediator compound or an enzyme electrochemically coupled by the said mediator compound, and,
(b) biotin,
wherein binding of the probe nucleic acid sequence to the target nucleic acid sequence modifies the electrochemical coupling between the mediator compound and the enzyme.

According to a third aspect of the present invention there is provided a method of assay for nucleic acids wherein an electrode is placed in contact with an enzyme and a substrate of the enzyme, and a mediator compound is associated with the enzyme to transfer charge from the enzyme to the electrode as the conversion of substrate into produce proceeds, and, a probe nucleic acid sequence is linked to either the enzyme or the mediator compound, whereby the activity the enzyme and the mediator compound and hence the quantity of charge being transferred to the electrode is modified by the presence or absence of a complementary target nucleic acid sequence bound to the probe nucleic acid sequence.

The general comments as to the nature of the mediator, enzyme, methodology and apparatus given in respect of the first aspect of the invention apply equally well to these second and third aspects which should be read accordingly.

The basis of the present invention is that a current passes in response to the presence of an electrochemically active substance or "mediator" at an electrode surface, as described in our earlier patent applications, especially our European Patent Application 82.305597. The magnitude of the current passed varies either
(a) in proportion to the amount of DNA-probe/target-DNA complex formed, or
(b) as a perturbation of an existing steady state current which is either enhanced or diminished, in proportion to the quantity of DNA-probe/target-DNA complex formed.

In one preferred embodiment of the present invention, the electrode exhibits reversible electron transfer with biotin-labled cytochrome-C. The biotin-labled cytochrome-C acts as a mediator compound, but can also bind to avidin as described in general terms above. Avidin or Streptavidin is added to the reaction mixture and binds to the mediator, reducing the transfer of charge to the electrode. The addition of biotin-labled nucleic acid (DNA or RNA) to the mixture sets up a competitive specific binding reaction between on the one hand a biotin Cytochrome-C (first ligand-mediator) complex with avidin (antiligand) and on the other hand an avidin (antiligand) complex with the biotin-labled nucleic acid (DNA or RNA) (second ligand). As the avidin (or streptavidin) concentration is fixed, an increase in the concentration of the avidin-biotin-nucleic acid complex will cause a corresponding increase in the concentration of the free Biotin Cytochrome-C species, which will cause a related increase in the rate of transfer of charge from the enzyme to the electrode surface.

Although the above embodiment of the invention has been described in terms of a first ligand linked to the mediator, it should be understood that the invention is also envisaged as being configured with the mediator linked to either the enzyme or the substrate.

In a further preferred embodiment of the present invention the electrode surface detects and measures an enzyme catalysed reaction in the presence of a mediator, which in a more preferable embodiment is cytochrome-C covalently linked to a nucleic acid probe. The electrochemical availability of the mediator is affected by the degree of homologous binding between the nucleic acid probe and the target DNA.

In a yet further preferred embodiment of the present invention, the electrode detects and measures, in the presence of a mediator, an enzyme-complex catalysed reaction. In a particular embodiment, the enzyme complex comprises a biotin-peroxidase-avidin complex which is capable of binding further biotin or biotin labled nucleic acid. A steady-state current is obtained using the peroxide substrate. This current decreases when biotin-labled nucleic acid is added to the assay mixture.

In each of the three embodiments described above there is a competitive reaction between the probe-containing species and the electrochemical system comprising the mediator, enzyme and substrate. The rate of charge transfer is perturbed by a lowering of the availability of the probe-containing species. Consequently, when a sample containing target nucleic acid is added to the assay system, the degree of homologous binding between the probe nucleic acid and the target is reflected in a lowering of the availability of the free probe containing species, and a corresponding change in the rate of charge transfer.

In a still further preferred embodiment of the present invention, the mediator is a ruthenium compound.

The rate of reduction of the ruthenium compound pentaammineisonicotinamineruthenium (III) was first noted to be high in 1970 by Taube. Since this time a quantity of work has been done with ruthenium compounds both in liquid systems and on electrodes, however the incorporation of a ruthenium compound into a charge transfer electrode is presented here for the first time.

Specific ruthenium compounds which are preferred in embodiments of the present invention include the following;

$[Ru(NH_3)_5py]^{3+,2+}$,
$[Ru(NH_3)_6]^{3+,2+}$,
$[Ru(NH_3)_5L]^{3+,2+}$,
where L is 4-aminomethylpyridine (AMP), or L is N-(4-picolinic)-benzamide (PBA)
$[Ru(NH_3)_5OH_2]^{3+,2+}$, and,
$[Ru(NH_3)_5Cl]^{3+,2+}$.

A method for attaching the first above listed compound to a graphite electrode is disclosed by Koval and Anson (as referenced above).

It is also envisaged that the present invention extends to novel conjugates of DNA or RNA and ruthenium derivatives. It has been known [Clarke and Taube Journal of the American Chemical Society 97, 1397–1403 (1975)] to prepare adducts of ruthenium compounds with xanthines, and it is therefore believed possible that the methods of the present invention may be extended to nucleotide derivatives which are ruthenium adducts.

According to a fourth aspect of the present invention there are provided kits of reagents and/or apparatus for carrying out the methods of assay for nucleic acids described, supra.

Figure 2:
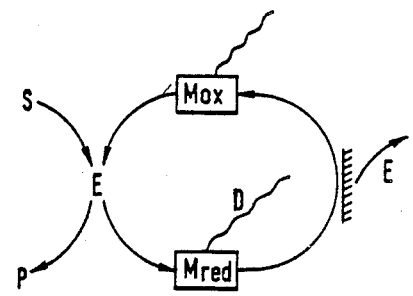
Figure 3:
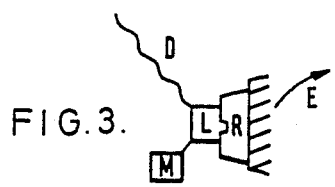
Figure 4:
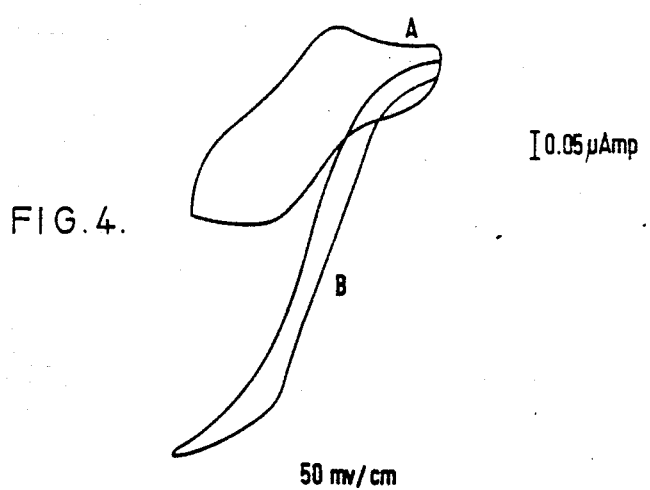

In order that the present invention may be further understood, it will be further illustrated by way of example with reference to the accompanying figures wherein;

FIG. 1; shows an assay protocol in which the nucleic acid is bound to the enzyme, FIG. 2; shows an assay in which the nucleic acid is bound to the mediator, FIG. 3; shows an assay in which the nucleic acid is bound to a linker which has an affinity for the electrode surface, FIG. 4a; shows the cyclic voltammogram of 2.8 mg biotin cytochrome-C in the presence of horseradish peroxidase.

FIG. 4b; shows the same as 4a on addition of 300 mM hydrogen peroxide,

FIG. 5; shows a y-t recorder trace of the current produced in the presence of 1.4 mg/ml of biotin-cytochrome C, 105 m/ml horseradish peroxidase, at a BPS 4,4-dipyridyldisulphide surface modified gold working electrode, FIG. 6; shows the cyclic voltammogram of $[Ru(NH_3)_5py]^{2+}$, with gold as a working electrode in the presence of 6 mM biotin-peroxidase avidin enzyme complex, FIG. 7; shows further details of FIG. 6, and, FIG. 8; shows a y-t plot of the catalytic current against time with the addition of biotinylated DNA to the assay mixture.

EXAMPLE 1

Enzyme Attached to DNA Probe

In FIG. 1, E is an enzyme, for example, glucose oxidase, which catalyses the conversion of a substrate S (for example glucose) to a product, P, (for example gluconolactone which then gives gluconic acid) and liberates electrons, e, which reduce the oxidised form of a mediator $M_{ox}$ (for example the ferricinium ion) to the reduced form, $M_{red}$ (for example ferrocene). $M_{red}$ is oxidised at the electrode G, the current passed is measured and is proportional to the amount of substrate S present.

Bound to the enzyme E by any suitable method is a DNA fragment, D, which may be either derived from a naturally occurring DNA sequence or may be synthetic. In the presence of an excess of the substrate S, a steady state current is obtained. A sample of DNA which is to be assayed for a particular target sequence complementary to the sequence of the DNA fragment D is converted to single strands by any suitable method, and then added to the reaction mixture.

If a target sequence complementary to the DNA fragment D is present in the mixture, it will bind to the fragment D and inhibit the enzymatic reaction of the enzyme E with the substrate S. Consequently the throughput of substrate S to product P will be reduced and the coupled reduction of $M_{ox}$ will be diminished. The change in the rate of reduction of $M_{ox}$ is reflected in a reduction of the current at the electrode G.

The change in current is proportional to the amount of the fragmented DNA D which is now bound to target DNA and hence to the amount of target DNA present.

EXAMPLE 2

Mediator Attached to DNA Probe

In example 2, the redox-active mediator M (in this example a substituted ferrocene) is attached directly (as shown in FIG. 2) to the fragmented DNA which is to be used as a probe. The formation of mediator-linked DNA-probe does not impede either the amperometric response of the mediator M nor the binding interaction of the mediator-DNA probe with the complementary target sequence contained in the DNA which is being assayed.

The amperometric response caused by the addition of the mediator-DNA probe to the assay mixture is measured. If genetic material in a single-stranded form to which the probe is complementary is present, the probe binds to the complementary sequence in the sample DNA. This greatly reduces or completely inhibits the amperometric response, that is, the complex of the mediator-DNA probe and the target DNA is not amperometrically active. The reduction in the initial amperometric response is in direct proportion to the amount of mediator-DNA probe/target DNA complex formed and hence to the amount of genetic material containing a sequence complementary to the known sequence of the mediator-DNA probe.

EXAMPLE 3

Mediator- and Linker-Attached to DNA Probe

In this example (as shown in FIG. 3) the mediator-DNA probe also contains one or more linker groups L, (biotin may for example be used).

The mediator-linker-DNA probe is in this exemplary method treated with the sample suspected of containing the single-stranded genetic material which is the target for the DNA probe and the mediator-linker-DNA probe binds to any complementary sequence present.

An electrode G on whose surface is present an electrochemically active material R, that recognises the linker group L, for example avidin labelled with ferrocene, is then immersed in the reaction mixture. The current measured on applying a potential is reduced on the binding of the electrochemically active material R to the mediator-linker-DNA probe/target-DNA complex. The reduction of the current is again in proportion to the amount of the added single-stranded sequence with a target sequence complementary to the known sequence of the DNA-probe.

EXAMPLE 4

System Comprising Biotin Cytochrome-C and Peroxidase

In this particular embodiment, the electrode exhibits reversible electron transfer with biotin-labled cytochrome-C. The biotin-labled cytochrome-C acts as a mediator compound, but can also bind to avidin as described in general terms above.

The addition of biotin-labled nucleic acid (DNA or RNA) to the mixture sets up a competitive specific binding reaction between on the one hand a biotin Cytochrome-C complex with avidin and on the other hand an avidin complex with the biotin-labled DNA.

As the avidin (or streptavidin) concentration is fixed, an increase in the concentration of the avidin-biotin-nucleic acid complex will cause a corresponding increase in the concentration of the free biotin Cytochrome-C species, which will cause a related increase in the rate of transfer of charge from the enzyme to the electrode surface.

As an example a gold electrode surface modified with 4,4-bipyridyl, or like material, was used. In this exemplary method the biotin-labelled cytochrome C acts as a mediator to an enzyme, in the present example, horseradish peroxidase.

The enzyme transfers charge between the mediator, (biotin cytochrome C in this case), and the substrate ($H_2O_2$), as shown by the catalytic current produced on addition of $H_2O_2$, as illustrated in FIGS. 4a and 4b.

Both the enzyme and the substrate are present in excess. The method operates by poising the potential of the cathode at a suitable, negative value, giving a resulting catalytic current which depends on the biotin-cytochrome C concentration.

Avidin or streptavidin is now added to the system. Some of the mediator complexes to the avidin, and the catalytic current consequently decreases. The addition of the biotin-containing DNA or RNA releases some of the biotin cytochrome C since the former competes for the avidin present. As a result the catalytic current increases in proportion to the added biotinylated DNA, as illustrated in FIG. 5.

Experimental conditions

A conventional three electrode system, was employed, wherein a 4,4-bipyridyldisulphide-coated gold electrode was used as the working electrode. Other components of the assay mixture were 0.05M phosphate buffer, pH 6.2; biotin-cytochrome C (SIGMA); 0.14–2.8 mg; $H_2O_2$ 300–80 mM; horseradish peroxidase 210 mg/ml; avidin 5–50 mg; biotin polyuridyl (BRL) 1–10 ul.

The cyclic voltammogram of biotin-cytochrome C (scan between −200 and +200 mV) does not change when the enzyme horseradish peroxidase is added to the cell, as can be seen from FIG. 4a.

The addition of substrate ($H_2O_2$) results in a dramatic change due to the catalytic current, as shown in FIG. 4b.

The electrode is poised at a reduction potential as is shown generally in FIG. 5 the addition of substrate as shown at 5a, produces the catalytic current which depends on the biotin cytochrome C concentration.

In a second step, avidin is added to the assay system; the addition of the same amount of substrate results in reduced catalytic current because some of the biotin-cytochrome C is complexed, as shown in FIG. 5b.

In a third step as shown in FIG. 5c, biotin-DNA and RNA is added to the system; addition of the same amount of $H_2O_2$ increased the catalytic current thus showing a dependence on the probe being present.

EXAMPLE 5

Activated Calf Biotin-Lablled Calf-Thymus DNA

This example employs an electrode surface which detects and measures in the presence of a mediator, which in this case is biotin cytochrome C covalently attached to DNA or RNA or cytochrome C covalently attached to DNA or RNA, an enzyme-catalysed reaction.

The catalytic current in the presence of excess enzyme or substrate is a measure of the biotin-cytochrome C-DNA(BCDNA), or cytochrome DNA(CDNA) present in the electrochemical cell.

Experimental conditions for preparation of activated BC Labelled calf thymus DNA A cytochrome C bridge was used to attach the biotin to DNA, (Manning et al) Biotin-labelled cytochrome C (commercially available from SIGMA) 5 mg was added to 4 mg of activated calf thymus DNA (Pharmacia PL Biochemicals) in 0.1M triethanolamine (TEA) pH 7.8.

1.2 ml of 6% formaldehyde was added in the same buffer for cross-linking, and the mixture was incubated at 37° for an hour. The formaldehyde was removed by extensive dialysis.

Sodium chloride was added to the sample to give a final concentration of 1M (to dissociate any cytochrome C which was not covalently bound).

The solution was fractionated on an FPLC gel filtration column using Sepharose 6B. The fractions were detected at 254 nm. The extinction coefficient of 25 $cm^2$/mg for DNA at 260 nm, and 7.7 $cm^2$/mg for biotin-cytochrome C at 410 nm were used to calculate the nucleotide to cytochrome C ratio and was found to be approximately 20:1 in the product.

The BCDNA or CDNA acts in the electrochemical cell as a mediator to horseradish peroxidase. In the presence of substrate the catalytic current is a measure of the amount of BCDNA or CDNA present or the amount of hybrid present.

The electrode is poised at a reducing potential. The catalytic current indicates the presence of the biotin cytochrome C DNA (or RNA) or cytochrome C DNA (or RNA).

A standard three electrode system employing a 4,4 bipyridyldisulphide-coated gold working electrode was used in 0.05M phosphate buffer at pH 6.2. The mediator is biotin-cytochrome-DNA (BCDNA) in this example, although it is envisaged that any other electrochemical label attached through a cytochrome bridge which mediates between horseradish peroxidase and an electrode could be used.

If cytochrome-C is used, its concentration should be not more than 300 uM because of the danger of bleaching the cytochrome-C at higher concentrations.

EXAMPLE 6

Nick Translation of Biotin Lablled 'Phage Lamda DNA

In this exemplary method, use is made of an electrode surface which can detect or measure, in the presence of a mediator, an enzyme complex-catalysed reaction. In this example the enzyme complex consists of biotin peroxidase-avidin in a proportion such that it can bind additional biotin or a biotin containing material such as biotin-labelled DNA or RNA.

A steady-state current is obtained using the biotin peroxidase-avidin complex in the presence of $H_2O_2$ and a mediator such as cytochrome C, a ferrocene compound or, in the examples shown herein [Ru(NH$_3$)-5py]$^{2+}$. The electrode is poised at a negative potential. The substrate, $H_2O_2$ is present in high excess. The current increases when biotin labelled DNA or RNA is added to the cell. The biotin DNA may be either in solution or is attached to a membrane.

At a limiting concentration of the biotin peroxidase-avidin complex and excess mediator and substrate, if the electrode poised at a suitable potential, (in this particular instance negative with respect to a saturated calomel electrode) a steady state current is obtained which is proportional to the enzyme concentration.

From this point the experiment presented here by way of example was performed according to two different experimental protocols, that is either by the addition of;

(a) Biotin DAN or Biotin RNA added in solution
(b) Immobilised biotin DNA or biotin RNA, In both instances the nucleic acid reacts with the enzyme complex, and gives a current increase which is proportional to, and acts as a measure of, the added Biotin DNA or RNA.

Experimental conditions for the Nick translation of biotin-labelled Phage Lamda DNA Sonicated phage Lamda DNA was nick translated in the presence of biotin-11-dUTP, according to the BRL technical information protocol using their nick translation reagent system, the reagents employed being as follows;

(1) 10 ul solution of the mixture of 0.2 mM dATP, dCTP, dGTP in 500 mM Tris pH7.8 50 mM MgCl$_2$, 100 mM 2-mercaptoethanol, and 100 mg/ml nuclease-free BSA.
(2) 4 ug of Lamda phage DNA in 0.1 mM EDTA, 10 mM Tris pH7.5 and 100 mM sodium chloride.
(3) 10 ul of biotin-11-dUTP in 0.4 mM in 100 mM Tris pH 7.5.

The volume was made up to 90 ul and the reaction mixture was carefully mixed.

(4) 10 ul DNA polymerase was added to the mixture, 0.4 units per ul, 40 pg per ml DNAase I in 50 mM Tris pH7.5, 5 mM magnesium acetate, 1 mM 2-mercaptoethanol, 0.1 mM phenylmethyl-sulfonylfluoride, 50% glycerol, and 100 ug per ml nuclease free BSA.

The mixture was incubated at 15° C. for 90 minutes. The reaction was stopped by adding 10 ul 300 mM EDTA. The purification of the biotin-labelled DNA was carried out according to the "Spin column Procedure" for Maniatis et al [Mantiati, Fritsor and Sambrook, Molecular Cloning a laboratory manual, 1982, Cold Spring Harbor Labs 466–467].

A 1-ml disposable syringe was used, which was plugged with a small amount of glass wool. A 0.9 ml bed volume of Sephadex was equilibrated with 0.15M sodium chloride, and 0.015M sodium citrate at pH7.0 was packed in the syringe, and spun on a bench centrifuge, several times until the packed volume, 0.9 ml. 0.1 ml of buffer was then added to the syringe which was then spun at the same speed and for the same time.

Finally, the nick translation mixture was added in 0.1 ml and re-centrifuged at exactly the same speed and time and the 100 ul of effluent was collected in a de-capped Eppendorf tube, which contained the biotin-labelled phage Lambda DNA. The biotin-labelled phage Lamda DNA BRL, probed, nick translated, as above, and biotin cytochrome C-labelled activated calf thymus DNA were attached to the nitrocellulose membrane by heating at 80° C. for 2 hours in a vacuum oven

EXAMPLE 7

Electrochemical Detection of Biotin-Lablled Lamda DNA

This experiment was performed in two ways, with DNA in solution and the DNA bound to a nitrocellulose membrane.

In both cases the assay system comprised a gold electrode in a 0.7 ml volume cell The reagents employed for this example were;
0.05 M phosphate buffer pH 6.2
Mediator
  (a) 0.15 mM ferrocene monocarboxylic acid
  (b) 0.16 mM $[Ru(NH_3)_5]Pyr^{2+}$
Biotin-peroxidase-avidin enzyme complex concentration 60 nM–0.6 nM as stated.
8.8 mM $H_2O_2$ as substrate.

The formation of enzyme complex was accomplished as follows: Vecta Stain ABC (Seralab) was used under their recommended conditions; 50 ul of biotin-peroxidase 5 mg/ml was incubated with 50 ul of avidin 1 mg/ml in 1 ml assay buffer containing 0.1% Tween 20 for 30 minutes. The further dilutions were made in the assay buffer containing 0.1% Tween 20.

EXAMPLE 7a

USE OF FERROCENE MONOCARBOXYLIC ACID

When ferrocene monocarboxylic acid was used as a mediator, the catalytic current was linear under the condition from 60 nM to 6 nM enzyme concentration giving a catalytic current in the range of 0.8–0.7 mA.

EXAMPLE 7b

USE OF RUTHENIUM COMPLEX AS A MEDIATOR

When $[pyRu(NH_3)_5]^{2+}$ was used as mediator, the catalytic current was approximately tenfold larger than in the previous case, therefore it was the choice in the three subsidiary experiments described by way of example below.

EXAMPLE 7c

ENZYME CONCENTRATION 6.0 nMOLAR

In this example the enyzme concentration was 6 nM. In the presence of $H_2O_2$ a steady state catalytic current was observed, as shown in FIG. 8a.

When biotin labelled phage Lamda DNA (200 ng) was added to the electrochemical cell the steady state catalytic current decreased. This is illustrated in FIG. 8b.

Further injection of $H_2O_2$ still results in a catalytic current. The result shows that the biotin-DNA complexes some of the biotin avidin enzyme complex, but still there is a high excess of the enzyme complex present which did not bind to the biotin DNA.

EXAMPLE 7d

ENZYME CONCENTRATION 0.6 nMOLAR

This example follows the lines of the previous example the only change being in the enzyme complex concentration, which is 0.6 nM in this case.

The catalytic current, as shown in FIG. 7b, characteristic of this enzyme complex concentration drastically changes, as shown in FIG. 7c, after addition of biotin DNA (200 ug). With further $H_2O_2$ injection the current remains at a decreased level as illustrated in FIG. 7D.

EXAMPLE 7e

DNA IMMOBILIZED ON MEMBRANE

A catalytic current is obtained with $H_2O_2$ substantially as described above. The biotin-labelled DNA immobilised on a nitrocellulose membrane, was added to the cell in the range of 0.5 ug–0.2 ug of DNA. After 10 minutes incubation with the biotin DNA membrane a further $H_2O_2$ injection did not induce any catalytic current, as shown by FIG. 7e, thus indicating that the enzyme complex binds to the biotin DNA present on the membrane, and charge transfer is therefore inhibited.

We claim:

1. An assay for determining a target nucleic acid sequence which comprises the steps of:
   (a) providing a probe material comprising,
     (i) a sequence of nucleic acids complementary to a given target sequence and,
     (ii) a first ligand chemically linked thereto and capable of a specific binding reaction with an antiligand;
   (b) contacting the said probe material with an assay system comprising,
     (i) a mediator, enzyme, substrate system capable of transferring charge to an electrode surface when the enzyme is catalytically active, and
     (ii) a second ligand chemically linked to one of said mediator, enzyme or substrate, wherein the second ligand is capable of competing with the first ligand for binding with the antiligand, and
     (iii) said antiligand;
     whereby said first ligand competes with said second ligand in a specific binding reaction with the antiligand, the extent of binding of said second ligand to said antiligand being reflected in the charge which said system transfers to said electrode surface;
   (c) contacting the above system with a solution suspected of containing the said target sequence whereby the binding of any of the said target sequence present in the solution to the probe affects the availability of the first ligand to compete with said second ligand to bind said antiligand and therefore alters the rate of charge transfer to the electrode and
   (d) measuring said charge transfer and relating said measurement to the determination of said target nucleic acid sequence.

2. The assay of claim 1, wherein the nucleic acid is deoxyribonucleic acid.

3. The assay of claim 1, wherein the nucleic acid is ribonucleic acid.

4. The assay of claim 1, wherein the specific binding reaction between either the first or the second ligand on the one hand and the antiligand on the other hand is characteristic of the specific binding reaction between a pair of reagents or derivatives thereof selected from the group of pairs consisting of: biotin and avidin, antigen and antibody, hormone and receptor, lectin and carbohydrate, cofactor and enzyme, and complementary nucleic acid strands.

5. The assay of claim 4, wherein both the first ligand and the second ligand are biotin or derivatives thereof and the antiligand is avidin or a derivative thereof.

6. The assay of claim 1, wherein the mediator is an organometallic compound.

7. The assay of claim 6, wherein the mediator comprises at least one organic ring, which is characterised by at least two double bonds that are conjugated and a metal atom in electron-sharing contact with each of the rings.

8. The assay of claim 7, wherein the metal is a transition metal.

9. The assay of claim 8, wherein the metal is selected from the group consisting of iron, chromium and ruthenium.

10. The assay of claim 9, wherein the mediator is a ferrocene.

11. The assay of claim 1, wherein the mediator is selected from the group consisting of viologens, polyviologens, phenazines, ferricyanide and derivatives thereof, metalloporphyrins and one-dimensional conductors.

12. The assay of claim 1, wherein the mediator is a carboborane.

13. The assay of claim 1, wherein the mediator is a ruthenium compound.

14. The assay of claim 10, wherein the mediator is selected from the group consisting of: ferrocene; chloroferrocene; methyl-trimethylaminoferrocene; 1,1-dimethylferrocene; 1,1'-dicarboxyferrocene; vinylferrocene; trimethylaminoferrocene; 1,1'dimethylferrocene; polyvinylferrocene; ferrocene monocarboxylic acid; hydroxyethylferrocene; acetoferrocene; and 1,1'-bishydroxymethyl ferrocene.

15. The assay of claim 11, wherein the mediator is a cytochrome.

16. The assay of claim 15, wherein the mediator is cytochrome-C.

17. The assay of claim 11, wherein the mediator is 7,7,8,8-tetracyano-p-quinodimethane.

18. The assay of claim 1, wherein the mediator is confined to an electrically conductive surface.

19. The assay of claim 1, wherein the enzyme is a non-oxygen specific flavoprotein.

20. The assay of claim 19, wherein said flavo-protein is selected from the group consisting of methanol dehydrogenase (EC 1.1.99.8) pyruvate oxidase (EC 1.2.3.3), xanthine oxidase (EC 1.2.3.2.2), sarcosine oxidase (EC 1.5.3.1), lipoamide dehydrogenase (EC 1.8.1.4), glutathione reductase (EC 1.6.4.2), carbonmonoxide oxidoreductase (EC 1.2.99.2), glucose oxidase, glycolate oxidase (EC 1.1.3.1) L-amino acid oxidase (EC 1.4.3.2) and lactate oxidase.

21. The assay of claims 1, wherein the enzyme is a quinoprotein.

22. The assay of claim 21, wherein said quino-protein is selected from the group consisting of glucose dehydrogenase, alcohol dehydrogenase and methanol dehydrogenase.

23. The assay of claim 1, wherein the enzyme is confined to an electrically conductive surface.

24. The assay of claim 1, wherein the enzyme is a haem-containing enzyme.

25. The assay of claim 24, wherein the haem-containing enzyme is chosen from the group consisting of lactate dehydrogenase yeast cytochrome-C peroxidase and horseradish peroxidase.

26. The assay of claim 1, wherein the enzyme is cuproprotein.

27. The assay of claim 26, wherein the cuproprotein is galactose oxidase.

28. The assay of claim 1, wherein the electrode is made of a material chosen from the group consisting of; gold, platinum, silver, carbon or a one-dimensional conductor.

29. A method of assay for determining a target nucleic acid sequence comprising: (a) providing, (i) an electrode in contact with an enzyme and a substrate of the enzyme, and a mediator compound associated with the enzyme to transfer charge from the enzyme to the electrode as the conversion of substrate into product proceeds, and (ii) a probe nucleic acid sequence complementary to said target sequence which is linked to either the enzyme or the mediator compound; (b) measuring a modification in the activity of the enzyme and the mediator compound and hence the quantity of charge being transferred to the electrode resulting from the binding of said target sequence to the probe nucleic acid sequence, and (c) relating said measurement to the determination of said target nucleic acid sequence.

30. The assay of claim 29, wherein the mediator compound, is selected from the group consisting of; transition metal compounds, metalloporphyrins, phenazines, carbon-boron compounds and viologens.

31. The assay of claim 30, wherein the mediator compound is biotin-labeled cytochrome-C.

32. The assay of claim 30, wherein said mediator is biotin labeled and either avidin or streptavidin is added and binds to the mediator, thereby reducing the transfer of charge to the electrode.

33. The assay of claim 29, wherein the electrode detects and measures, in the presence of a mediator, an enzyme-complex catalysed reaction.

34. The assay of claim 33, wherein the enzyme complex comprises a biotin-peroxidase-avidin complex.

35. The assay of claim 34, wherein the enzyme complex is capable of binding further biotin or biotin labeled nucleic acid.

36. The assay of claim 31, wherein either avidin or streptavidin is added and binds to the mediator, thereby reducing the transfer of charge to the electrode.

37. The assay of claim 31, wherein the electrode detects and measures, the presence of a mediator, an enzyme-complex catalysed reaction.

38. A nucleic acid probe for establishing the presence or copy number of a given target sequence in a single-stranded nucleic acid molecule, said nucleic acid probe being linked to
(a) either a metallocene mediator compound or an enzyme electrochemically coupled to an electrode by a metallocene mediator compound, and,
(b) biotin,
wherein binding of the probe nucleic acid to the target sequence modifies the electrochemical coupling between the metallocene mediator compound and the enzyme.

39. The nucleic acid probe of claim 38, wherein the mediator is immobilized on a surface.

40. The nucleic acid probe of claim 39, wherein the surface comprises nitrocellulose.

41. A nucleic acid probe comprising:
(a) a nucleic acid strand complementary to a target nucleic acid sequence, and
(b) a metallocene mediator chemically linked thereto, wherein said mediator transfers charge from a catalytically active enzyme to an electrode.

42. The probe of claim 41, wherein the mediator compound, is selected from the group consisting of; transition metal compounds, metalloporphyrins, phenazines, carbon-boron compounds and viologens.

43. The probe of claim 42, wherein the mediator is cytochrome-C.

44. The probe of claim 42, wherein the mediator is ferrocene.

45. The probe of claim 42, wherein the mediator is a ruthenium compound.

46. The probe of claim 45, wherein the mediator comprises $[Ru(NH_3)_5py]^{2+}$.

47. A kit of reagents for use in an assay to determine a target nucleic acid sequence comprising the nucleic acid probe of claim 41; an enzyme electrochemically coupled to an electrode by a mediator linked to said nucleic acid probe; and a substrate of said enzyme, wherein conversion of said substrate to product by said enzyme associated with said mediator transfers charge from said enzyme to said electrode.

* * * * *